United States Patent [19]
Wächter et al.

[11] Patent Number: 6,020,384
[45] Date of Patent: Feb. 1, 2000

[54] PROCESS FOR THE MANUFACTURE OF FLAVANOLIGNAN PREPARATION WITH IMPROVED RELEASE AND ABSORBABILITY, COMPOSITIONS OBTAINABLE THEREBY AND THEIR USE FOR THE PREPARATION OF PHARMACEUTICALS

[75] Inventors: Wilfried Wächter, Bergisch Gladbach; Helga Zaeske, Overath, both of Germany

[73] Assignee: Madaus AG, Cologne, Germany

[21] Appl. No.: 09/247,612

[22] Filed: Feb. 10, 1999

Related U.S. Application Data

[62] Division of application No. 08/976,771, Nov. 24, 1997, Pat. No. 5,906,991, which is a division of application No. 08/587,494, Jan. 17, 1996, abandoned.

[30] Foreign Application Priority Data

Jan. 18, 1995 [DE] Germany ............................ 195 01 266

[51] Int. Cl.[7] ........................ A61K 31/79; A61K 35/78; A61K 31/35
[52] U.S. Cl. ........................................ 518/452; 428/195.1
[58] Field of Search ........................ 424/195.1; 514/452

[56] References Cited

U.S. PATENT DOCUMENTS 4,081,529  3/1978  Crippa ........................................ 424/80

Primary Examiner—Frederick Krass
Attorney, Agent, or Firm—Fulbright & Jaworski, LLP

[57] ABSTRACT

The present invention provides a process for the production of a flavanolignan preparation with an improved liberation in comparison with one of the pure flavanolignans, characterised in that a) an aqueous-alcoholic solution of pharmaceutically-acceptable carrier materials and wetting agents is prepared, a flavanolignan is suspended in this solution and the mixture obtained is heated to the boiling temperature in order to form a clear solution or b) a flavanolignan and a wetting agent is suspended in alcohol, the suspension obtained is heated with stirring up to the formation of a clear solution, this is mixed with an aqueous solution of pharmaceutically-acceptable carrier materials and the mixture obtained is heated with stirring until a clear solution is present and that subsequently the clear solution obtained according to a) or b) is concentrated for the formation of a co-precipitate, filtered and the resulting co-precipitate dried in a vacuum. The flavanolignan preparation can be used as medicaments for the treatment and prophylaxis of liver diseases and also as liver protection agents for the avoidance of damage by medicaments, drugs and alcohol.

5 Claims, 2 Drawing Sheets

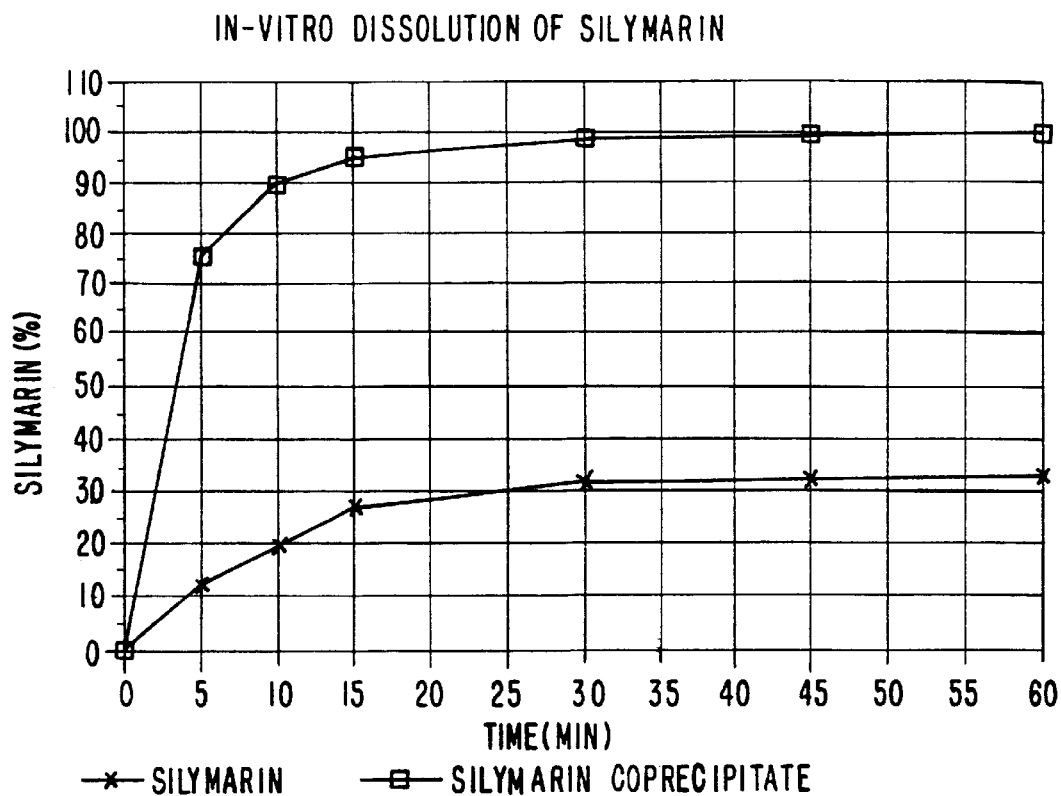
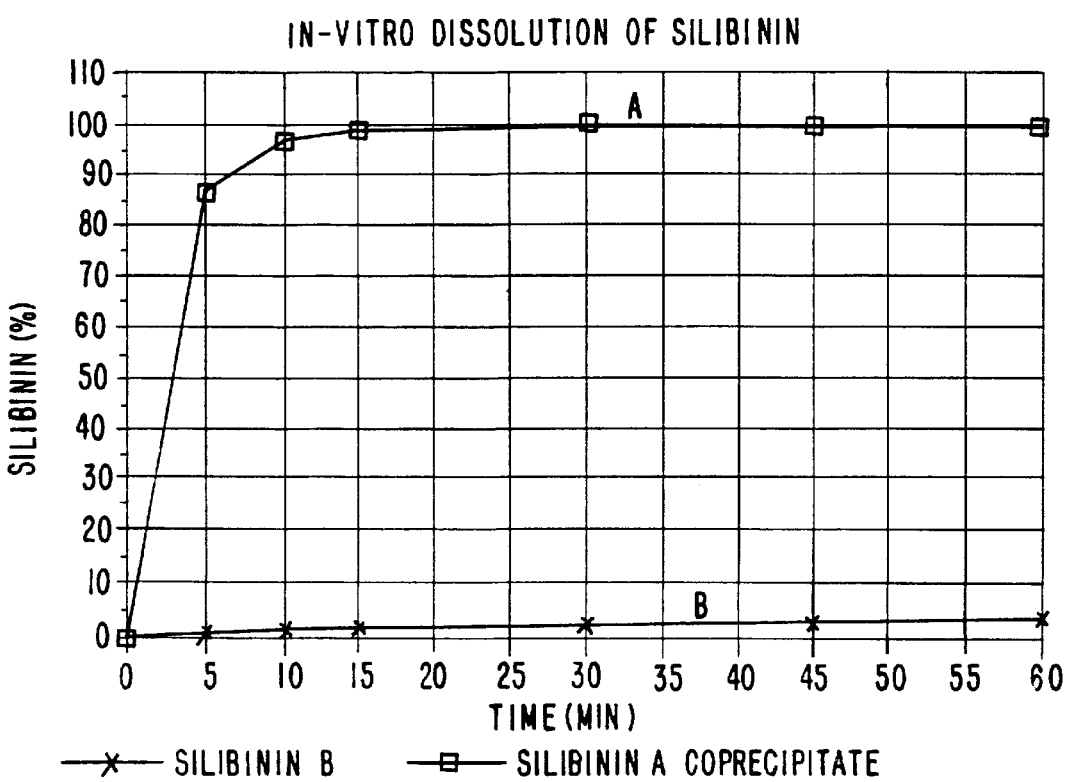

PROCESS FOR THE MANUFACTURE OF FLAVANOLIGNAN PREPARATION WITH IMPROVED RELEASE AND ABSORBABILITY, COMPOSITIONS OBTAINABLE THEREBY AND THEIR USE FOR THE PREPARATION OF PHARMACEUTICALS

This is a divisional of U.S. patent application Ser. No. 08/976,771 filed Nov. 24, 1997, now U.S. Pat. No. 5,906,991, which is a divisional of U.S. patent application Ser. No. 08/587,494, filed Jan. 17, 1996, now abandoned, both of which are incorporated herein by reference.

The present invention is concerned with a process for the production of flavanolignan preparations with a liberation and resorbability improved in comparison with pure flavanolignans, preparations obtainable according to this process and pharmaceutical compositions containing them for use in the therapy and prophylaxis of liver diseases.

Silymarin obtained from lady's thistle (Silybum marianum, Compositae) has been known for a long time. Processes for obtaining polyhydroxyphenylchromanones (silymarins I–IV) and medicaments containing them as mixtures are described in DE-C3-19 23 082.

From this Patent Specification, it is also known that silymarin accounts for 80 to 85 mol. % of the active material as commercial product. Silymarin is a mixture of silibinin, isosilybin, silydianin and silychristin, it being a mixture of molecular mixed isomers with the same sum formula $C_{25}H_{22}O_{10}$. Silibinin, isosilybin, silydianin and silychristin are flavolignans in which taxifolin is linked with coniferyl alcohol.

From DE-C2-29 14 330 is known a process for obtaining pure silymarin (silymarin I–IV), silymarin (I–IV) obtained according to this process with at least 90% purity and the use thereof for the treatment of liver diseases.

BACKGROUND OF THE INVENTION

Furthermore, from DE-C2-35 37 656 is known a process for obtaining isosilybin-free silibinin, as well as medicaments containing this.

It is known that flavanolignans are, as a rule, insoluble or not very soluble in water. Because of this dissolving behaviour, the rate of liberation of these compounds and thus also the bioavailability thereof and the resorbability thereof in the body of humans and mammals treated therewith is unsatisfactory. Therefore, in the past, the attempt has been made, in the case of the flavanolignans, to bring about a molecular change by treatment or reaction with appropriate chemical agents and thus to convert them into derivatives with improved water-solubility and increased rate of liberation. The derivatives formed in this manner include, for example, adducts with, inter alia, cyclodextrin, for example silibinin-β-CD (CD=cyclodextrin); complex compounds with, for example, phosphatidylcholine or with certain aminosugars; esters, especially with dicarboxylic acids, as well as inclusion compounds. It is a disadvantage in the case of these derivatives that, in individual cases, the flavanolignan in question is bound to a chemical compound which can act physiologically as a foreign substance and possibly bring about undesired side reactions or impair the effectiveness of the flavanolignan. In the case of the production of adducts, complexes of derivatives, the γ-pyrone ring of the flavanone part is often opened, for example in an alkaline medium. Furthermore, in the case of the mentioned derivatives, the danger also exists that, in the case of the administration of a flavanolignan modified or derivatized in the mentioned way, this is admittedly better resorbed but brings about an action which is substantially different from that expected and desired for the flavanolignan.

It is an object of the present invention to provide flavanolignan preparations which do not have a binding of the flavanolignans to foreign compounds and possess a good, high rate of liberation by means of which a sufficient bioavailability and a good resorption by the body of the treated individual is ensured after administration thereof. These flavanolignan preparations are to have the desired and expected actions of the flavanolignans in question and to display none of the side effects or changes of their specific effectiveness or of their activity spectrum to be attributed to the binding to foreign compounds, i.e. the agents used in the above-described derivatization.

BRIEF DESCRIPTION OF THE DRAWINGS

FIG. 1 is a graph of the in-vitro dissolution of silymarin vs. the silymarin co-precipitate of the invention;

FIG. 2 is a graph of the in-vitro dissolution of silibinin vs. the silibinin co-precipitate of the invention.

DETAILED DESCRIPTION OF THE INVENTION

Figure 3:
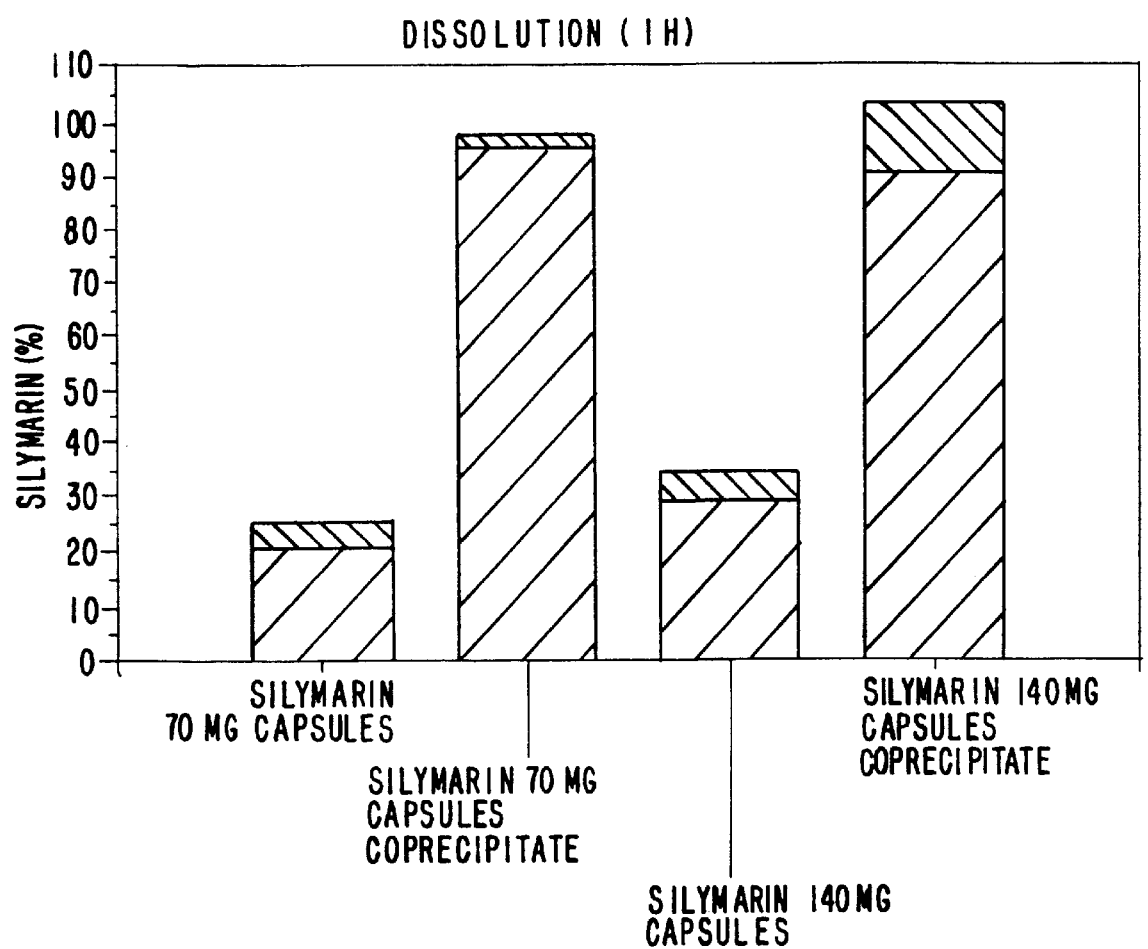
FIG. 3 is a graph showing the in-vitro dissolution of silymarin 70 mg and 140 mg capsules vs. silymarin co-precipitate 70 mg and 140 mg capsules at 1 hour.

Thus, according to the present invention, there is provided a process for the production of a flavanolignan preparation with an improved liberation in comparison with that of the pure flavanolignan, wherein a) there is prepared an aqueous alcoholic solution of pharmaceutically-acceptable carrier materials and wetting agents, a flavanolignan is suspended in this solution and the mixture obtained is heated to the boiling temperature in order to form a clear solution or b) a flavanolignan and a wetting agent are suspended in alcohol, the suspension obtained is heated, while stirring, for the formation of a clear solution, this is mixed with an aqueous solution of pharmaceutically-acceptable carrier materials and the mixture is heated, with stirring, until a clear solution is obtained and wherein subsequently the clear solution obtained according to a) or b) is concentrated for the formation of a co-precipitate, filtered and the resultant co-precipitate dried in a vacuum.

Especially preferred is the production of flavanolignan preparations in which the flavanolignan is silymarin or silibinin and especially a powdered silymarin co-precipitate and/or a powdered silibinin co-precipitate.

Preferably used pharmaceutically-acceptable carrier materials include water-soluble sugar derivatives, for example mono- and disaccharides, polyglycose, polymaltose, sugar alcohols and/or celluloses and mixtures thereof. As mono- and disaccharides, there are especially preferred dextrose, fructose, galactose, glucose, lactose, mannose, maltose, saccharose, xylose, mannitol and sorbitol. Of the celluloses, hydroxyethyl-starch, carboxymethyl-cellulose and sodium carboxymethyl-starch are preferred. The amount of this group can be 2 to 80% and preferably 5 to 20%, referred to the solid materials used in the end product, including the active material. The preferred carrier materials are used, together with pharmaceutical wetting agents and pharmaceutical carrier materials, for dispersed systems.

Preferred pharmaceutical wetting agents include polyoxyethylene derivatives of sorbitan esters, for example polysorbates 20, 40, 60 and 80 and especially polysorbate 80, as well as also sorbitan esters of fatty acids, for example sorbitan laurate, oleate, palmitate and sesquioleate. The amounts thereof can be 0.1 to 5% and preferably 0.5 to 2%.

Preferred pharmaceutical carrier materials for disperse systems include polymers of 1-vinyl-2-pyrrolidone, especially poly-[(2-oxo-1-pyrrolidinyl)-ethylene], which is also called polyvidone. The amounts thereof can be 5 to 90% and preferably 20 to 50%.

According to production variant a), the pharmaceutically acceptable carrier materials, the pharmaceutical wetting agents and the pharmaceutical carrier materials for disperse synthesis are dissolved in the given ratio in aqueous alcohol and a flavanolignan suspended in this solution, the suspension being heated to the boiling temperature to form a clear solution. As previously described, production process b) is carried out correspondingly. Subsequently, a co-precipitate is formed by concentration, filtered off and dried in a vacuum.

In the case of the production of capsules from the finished product, a lubricant is added, for example magnesium stearate, the amount being 0.3 to 2% and preferably 0.4 to 0.8% of the final product.

The preparations obtainable by the above-described process and present in the form of a co-precipitate are characterised by a rate of liberation which is considerably higher than that of the pure active material and thus by a substantially improved bioavailability. The preparations are excellently resorbed in the body of the individual treated therewith and manifest the desired and expected physiological action for the flavanolignan in question. Therefore, they can be used as medicaments for the treatment of liver diseases and for the prophylaxis of liver damage and also as liver protection agents for the avoidance of damage by medicaments, drugs and alcohol.

EXAMPLES OF PREPARATION

Preparation of Silymarin Co-precipitate

A) Obtaining of Silymarin (Silymarin I–IV)

Silymarin was obtained by the process described in DE-C3-19 23 082, to which reference is here made. The product thereby obtained by the process according to U.S. Pat. No. 4,368,195, to which reference is here also made, was worked up to give silymarin (silymarin I–IV) with a purity of at least 90%.

B) Preparation of the Base Solution 2.63 kg mannitol 1.06 kg sodium carboxymethylstarch 0.415 kg polysorbate 80

12.895 kg polyvidone 626 1 ethanol (0.8) The mannitol, sodium carboxymethylstarch, polysorbate 80 and polyvidone were dissolved in the ethanol, with stirring and warming. The adjustment of the ethanol to the desired density was carried out with pure water.

C) Production and Preparation of the Feed Solution

Into the base solution produced in B were dosed 18 kg of the silymarin produced by the process described in A (calculated as dry substance). The mixture obtained was heated to the boiling point in order to obtain a clear solution. The clear solution was filtered over filter layers K 100 and kept ready for concentration in a storage vessel. The feed solution was kept at a temperature of >45° C.

2. Concentration

The feed solution was concentrated to one tenth of its volume under a vacuum in the course of 50 minutes in an evaporation plant at a maximum temperature of 60° C.

3. Drying

The concentrated material was dried in a vacuum drying cabinet at 70° C. and 1 mbar to a residual moisture content of <7%.

4. Grinding

The dried material was fine ground (nominal sieve residue >40 μm must be <1%.

5. Post-drying

Post-drying was carried out in a vacuum drying plant at 1 mbar and 70° C. until the limited proportion of solvent had been gone below.

The so-produced co-precipitate was investigated for the determination of the rate of liberation in vitro and for the determination of the bioavailability in vivo as described hereinafter.

Preparation of Silibinin Co-precipitate

A) Obtaining of Isosilybin-free Silibinin

Isosilybin-free silibinin was obtained according to the process described in DE-C2-35 37 656, to which reference is here made. The product thereby obtained contained 97 to 98.5% silibinin.

B) Preparation of the Base Solutions I+II

Base Solution I:

23.10 kg polyvidone and 2.316 kg lactose were suspended in 375 1 of pure water, whereupon the suspension was converted into a clear solution by stirring and heating.

Base Solution II:

3.75 kg silibinin (calculated on 100% silibinin) and 0.75 kg polysorbate 80 were suspended in 375 1 ethanol, whereupon the suspension was converted into a clear solution by heating and stirring.

C) Preparation of Working up of the Feed Solution

1. Preparation of the Solution

The base solutions I and II described in B were combined by mixing base solution I, with stirring, into base solution II, care thereby being taken that a clear solution resulted which was filtered over filter layers K 100 and kept ready in a storage vessel until concentrated. The feed solution was kept at a temperature of >45° C.

2. Concentration

The feed solution was concentrated to one twentieth of its volume over the course of 50 minutes in an evaporation plant at a maximum temperature of 60° C.

3. Drying

The concentrated material was dried in a vacuum drying cabinet at 70° C. and 1 mbar up to a residual moisture content of <7%.

4. Grinding

The dried material was finely ground (nominal sieve residue >40 μm must be <1%).

5. Post-drying

Post-drying was carried out in a vacuum drying plant at 1 mbar and 70° C. until the limited proportion of solvent had been gone below.

The so-produced co-precipitate was investigated for the determination of the rate of liberation in vitro and for the determination of the bioavailability in vivo as is described hereinafter.

Determination of the Rate of Liberation and Bioavailability of Silymarin, Silymarin Co-precipitate, Silibinin and Silibinin Co-precipitate The determination of the rate of liberation was carried out in vitro by means of a modified HPLC method; the bioavailability was determined in vivo by means of clinical experiments on healthy subjects.

The experimental results are explained on the basis of FIGS. 1 and 2 of the accompanying drawings, in which:

FIG. 1 is a comparison of the liberation of silymarin with the liberation of silymarin co-precipitate depending upon the time (min.), in graphical representation; and FIG. 2 is a comparison of the liberation of silibinin with the liberation of silibinin co-precipitate depending upon the time (min.), in graphical representation.

Determination of the Rate of Liberation of Silymarin, Silymarin Co-precipitate, Silibinin and Silibinin Co-precipitate in vitro For the determination of the percentage liberation of silymarin co-precipitate in comparison with pure silymarin, the two substances were stirred in an apparatus equipped with paddle mixers in a buffer solution (pH 7.5) at 37° C. for 60 minutes and subsequently centrifuged. The determination of the percentage liberation was carried out chromatographically by means of a newly developed HPLC method.

From FIG. 3 of the accompanying drawings, it can clearly be seen that the percentage liberation of silymarin co-precipitate is considerably higher than that of silymarin in the form of the pure active material. In the case of silymarin in the form of the pure active material in 140 mg capsules, it amounts to approximately 30% in the case of a range of spread, which is shown by the dark cross-hatching, of <10%, whereas the percentage liberation in the case of silymarin co-precipitate amounted to approximately 95% in the case of a range of spread of about 10%. These results are also confirmed in the liberation profile of silymarin and silymarin co-precipitate with the time in FIG. 1.

FIG. 2 of the accompanying drawings shows the liberation profile of silibinin and silibinin co-precipitate depending upon the time. On the abscissa is thereby given the time in minutes and on the ordinate the liberation in percentage. The carrying out of the experiment corresponded to that described in connection with the determination of the percentage liberation of silymarin and silymarin co-precipitate. From this Figure, it can be seen that the percentage liberation of silibinin co-precipitate exceeds that of the pure active material silibinin by a multiple. The curve (A) obtained from three series of measurements, which gives the liberation of the silibinin co-precipitate, lies—after a steep increase during the first five minutes—above the 90% level. On the other hand, the curve (B), also from three series of measurements, for the liberation of the pure active material silibinin lies below the 10% level, the rate of liberation of silibinin after 30 minutes thereby being below 5%.

Determination of the Bioavailability of Silibinin and Silibinin Co-precipitate in vivo In contradistinction to the earlier investigations, the clinical experiments were carried out with subjects suffering from liver diseases, for example cholecystectomised patients with bile-T drain or in the case of patients with external hepatitic diseases, and with randomly selected healthy volunteers.

In the investigations described in the following, six healthy male subjects were selected. In a fasting state, they were given single doses of 102, 153, 203 and 254 mg silibinin. The healthy volunteers were hospitalized, namely, from the evening before the medication until 50 hours after the administration. During the investigation, the healthy volunteers received standard meals and drinks. Furthermore, they were asked to avoid excessive bodily exertions and other activities in the open air during the investigation, including 24 hours before the medication, as well as to omit smoking and the consumption of xanthine-containing drinks, such as coffee, tea and chocolate.

The characteristics of the subjects and the scheme of administration are given in the following Table 1.

TABLE 1

Characteristics of the subjects and scheme of administration

| subject | age (years) | height (cm) | weight (kg) | administration sequence number of capsules | | | |
|---|---|---|---|---|---|---|---|
| 1 | 29 | 172 | 68 | 2 | 3 | 4 | 5 |
| 2 | 22 | 178 | 69 | 3 | 4 | 5 | 2 |
| 3 | 26 | 185 | 76 | 4 | 5 | 2 | 3 |
| 4 | 24 | 182 | 66 | 5 | 2 | 3 | 4 |
| 5 | 29 | 175 | 75 | 2 | 5 | 4 | 3 |
| 6 | 29 | 190 | 71 | 4 | 2 | 5 | 3 |

The determination of the active material concentration in the plasma and the excreted amount in the urine of the subjects was carried out by means of a specific HPLC method. As already mentioned, in comparison with previously known methods, this method is characterised by a substantially lower limit of detection. In the case of the known methods, this was approximately 50 ng/ml in the plasma, whereas the detection limit in the new method had a value lower by the factor of 10.

SUMMARY OF THE EXPERIMENTAL RESULTS

The carrying out of the clinical experiments and the concentration determinations took place as described previously and in conjunction with the following Table 2. The results are set out in Table 2, whereby, in this Table, the relative bioavailability of silibinin is compared with that of silibinin co-precipitate. The relative bioavailability is given in [ng*h/ml].

TABLE 2

AUC [ng + h/ml] for silibinin co-precipitate and silibinin after 4 oral administrations to healthy volunteers

| subject No. | silibinin co-precipitate | silibinin |
|---|---|---|
| 1 | 1364 | 421.6 |
| 2 | 1589 | 617.6 |
| 3 | 2637 | 697.4 |
| 4 | 3004 | 710.6 |
| 5 | 2448 | 629.3 |
| 6 | 5355 | 1292.0 |
| 7 | 2254 | 642.5 |
| 8 | 1531 | 615.5 |
| AV | 2523 | 703.3 |

AUC = relative bioavailability (usual abbreviation used in pharmaceutics for "area under curve", corresponding to the integral of the region bounded by a curve)
AV = average value Harmful actions were not observed, from which it follows that the silibinin co-precipitate, just like silibinin and silymarin, is also tolerated in high dosages.

It will be understood that the specification and examples are illustrative but not limitative of the present invention and that other embodiments within the spirit and scope of the invention will suggest themselves to those skilled in the art.

We claim:

1. A solid oral unit dosage form comprising a flavanolignan co-precipitate, a wetting agent and a pharmaceutically acceptable carrier material, where said flavanolignan co-precipitate is obtained by the process of:
   a) providing an aqueous-alcoholic solution of a pharmaceutically acceptable carrier material and a wetting agent, suspending a flavanolignan in the aqueous-alcoholic solution to form a mixture, heating the mixture to a boiling temperature to form a clear solution; or
   b) suspending a flavanolignan and a wetting agent in alcohol to form a suspension, heating the suspension with stirring to a clear solution, mixing the clear solution with an aqueous solution of a pharmaceutically acceptable carrier material to form a mixture, heating the mixture with stirring to form a clear solution; and
   c) subsequently concentrating the clear solution obtained according to a) or b) for the formation of a co-precipitate, filtering the concentrated solution to obtain a co-precipitate and drying the co-precipitate in a vacuum.

2. The solid oral unit dosage form of claim 1 wherein said flavanolignan co-precipitate is a powdered silymarin co-precipitate which is present in an effective amount.

3. The solid oral unit dosage form of claim 1 wherein said flavanolignan co-precipitate is a powdered silibinin co-precipitate which is present in an effective amount.

4. A solid oral unit dosage form comprising a flavanolignan co-precipitate, a wetting agent and a pharmaceutical carrier material, where said flavanolignan co-precipitate is obtained from a suspension comprising flavanolignan and a wetting agent in alcohol, where said dosage form is tolerated in humans when said flavanolignan co-precipitate is provided at a dosage corresponding to 700 mg flavanolignan.

5. The dosage form of claim 4 wherein said flavanolignan co-precipitate is a silibinin co-precipitate and wherein said dosage form is tolerated at dosages of about 100 mg to about 250 mg silibinin provided as silibinin co-precipitate per administration.

* * * * *

UNITED STATES PATENT AND TRADEMARK OFFICE
CERTIFICATE OF CORRECTION

PATENT NO. : 6,020,384
DATED : February 1, 2000
INVENTOR(S) : Wächter et al

It is certified that error appears in the above-identified patent and that said Letters Patent is hereby corrected as shown below:

In column 2, line 53, insert a comma after the word "example" to read as - - example, - -.

In column 3, line 2, insert a comma after the word "example" to read as - - example, - -.

In column 3, line 7, change "poly-1(2" to read as - - poly-[(2 - -.

In column 3, line 7, change "ethylene 1," to read as - - ethylene], - -.

In column 3, line 57, insert a new paragraph beginning with the word "The".

In the cover page, in the title, change "PREPARATION" to read as - - PREPARATIONS - -.

In the cover page, under the heading Assignee, change "Cologne" to read as - - Koeln - -.

In the cover page, under the section titled Foreign Application Priority Data, change "195 01 266" to read as - - 095 01 266.6 - -.

Signed and Sealed this

Eighth Day of May, 2001

Attest:

NICHOLAS P. GODICI

*Attesting Officer*   *Acting Director of the United States Patent and Trademark Office*